(12) United States Patent
Reinke et al.

(10) Patent No.: US 7,718,425 B2
(45) Date of Patent: May 18, 2010

(54) USE OF A B-CELL-DEPLETING ANTIBODY FOR TREATMENT OF POLYOMA VIRUS INFECTIONS

(75) Inventors: Petra Reinke, Berlin (DE); Hans-Dieter Volk, Berlin (DE); Markus Hammer, Berlin (DE); Nina Babel, Berlin (DE); Gana Bold, Berlin (DE)

(73) Assignee: Charité-Universitätsmedizin Berlin, Berlin (DE)

( * ) Notice: Subject to any disclaimer, the term of this patent is extended or adjusted under 35 U.S.C. 154(b) by 0 days.

(21) Appl. No.: 12/299,142

(22) PCT Filed: May 2, 2007

(86) PCT No.: PCT/EP2007/003878

§ 371 (c)(1),
(2), (4) Date: Mar. 16, 2009

(87) PCT Pub. No.: WO2007/128482

PCT Pub. Date: Nov. 15, 2007

(65) Prior Publication Data

US 2009/0175861 A1 Jul. 9, 2009

(30) Foreign Application Priority Data

May 2, 2006 (EP) .................................. 06009050

(51) Int. Cl.
*C12N 5/06* (2006.01)
(52) U.S. Cl. .......................................... 435/345; 435/5
(58) Field of Classification Search ........................ None
See application file for complete search history.

(56) References Cited

U.S. PATENT DOCUMENTS 6,605,602 B1  8/2003  Vats

FOREIGN PATENT DOCUMENTS

JP          09067397       3/1997

OTHER PUBLICATIONS

Ahuja, M. et al., "Polyoma Virus Infection After Renal Transplantation", vol. 71, No. 7, Apr. 15, 2001, pp. 896-899.
Seshan, S. et al., " Immunophenotyping of BK virus nephropathy and acute allograft Rejection: Potential Diagnostic and prognostic markers", Laboratory Investigation, vol. 82, No. 1, Jan. 2002, pp. 280A.
Sansonno, D. et al., "Monoclonal antibody treatment of mixed cryoglobulinemia resistant to interferon alpha with an anti-CD20", Blood, vol. 101, No. 10, May 15, 2003, pp. 3818-3826.
Roccatello, D. et al., "Long-term effects of anti-CD20 monoclonal antibody treatment of cryoglobulinaemic glomerulonephritis", Nephrology, Dialysis, Transplantation; vol. 19, No. 12, Dec. 2004, pp. 3054-3061.
Herman, J. et al., "Successful treatment with Rituximab of lymphoproliferative disorder in a child after cardiac transplantation", The Journal of Heart and Lung Transplantation, vol. 21, No. 12, Dec. 2002, pp. 1304-1309.
Brito-Babapulle, F. et al., "Progressive multifocal leucoencephalopathy (PML) following Rituximab-combination chemotherapy treatment", British Journal of Haematology, vol. 133, No. suppl. 1, Apr. 5, 2006, p. 36.
Chang, A. et al., "CD3 and CD20 immunohistochemistry of renal transplant biopsies with polyoma virus-associated nephritis or acute allograft rejection", Modern Pathology, vol. 16, No. 1, Jan. 1, 2003, p. 266A.

*Primary Examiner*—Ali R. Salimi
(74) *Attorney, Agent, or Firm*—Pearl Cohen Zedek Latzer, LLP

(57) ABSTRACT

The present invention relates to uses of a B-cell-depleting antibody for the treatment of a polyoma virus infection.

22 Claims, 5 Drawing Sheets

USE OF A B-CELL-DEPLETING ANTIBODY FOR TREATMENT OF POLYOMA VIRUS INFECTIONS

Figure 1A:
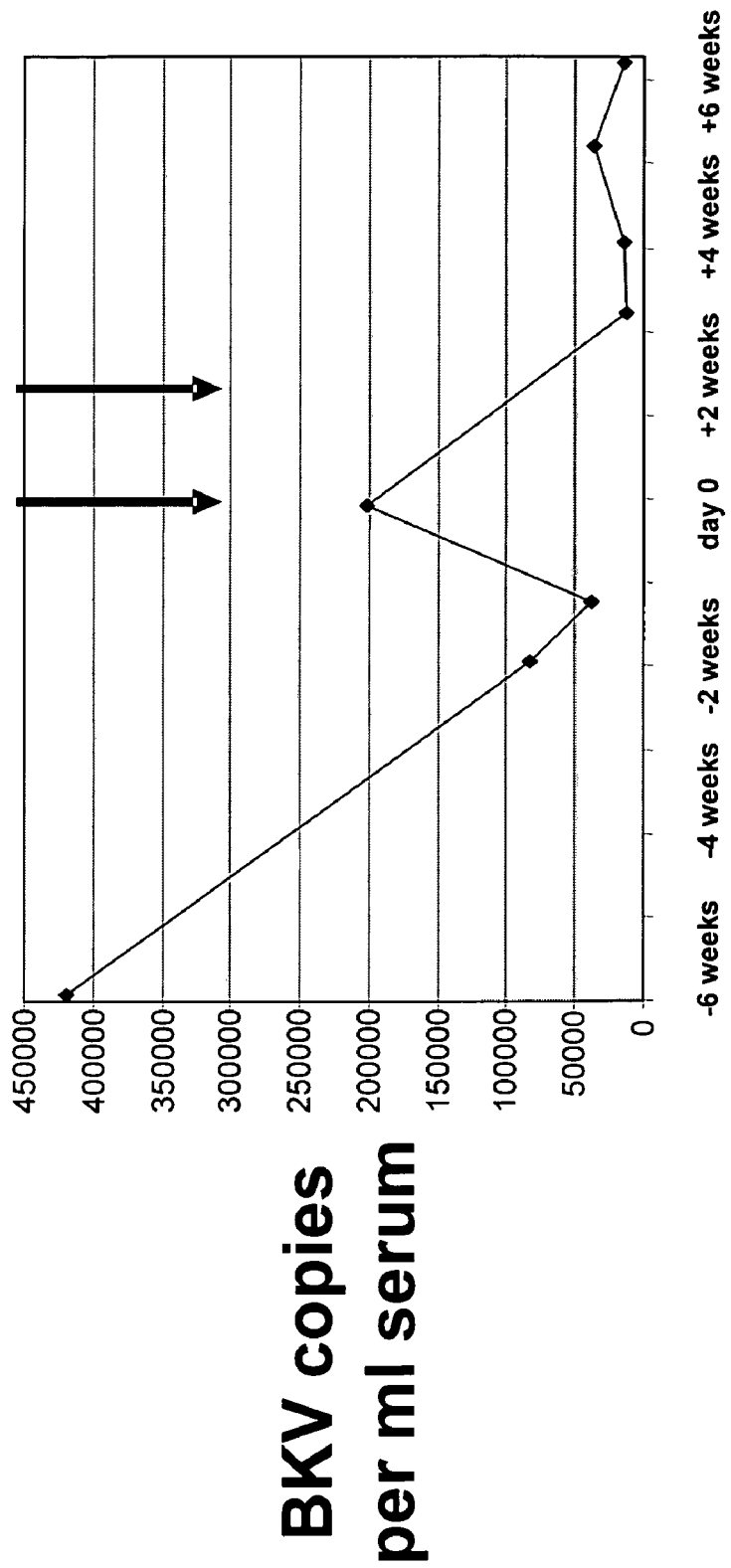
Figure 1B:
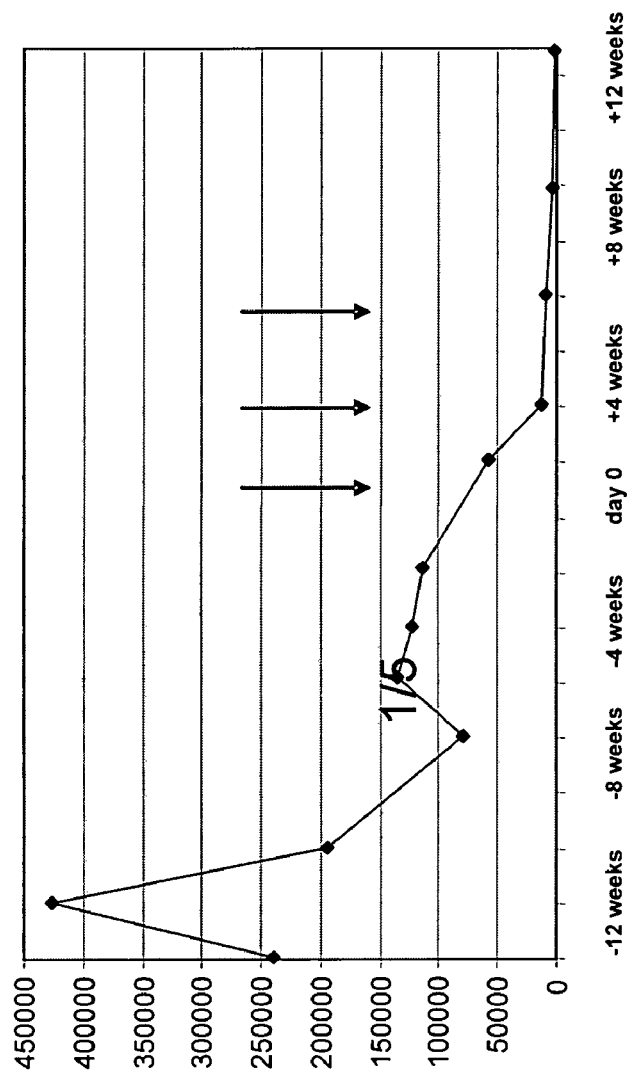
Figure 1C:
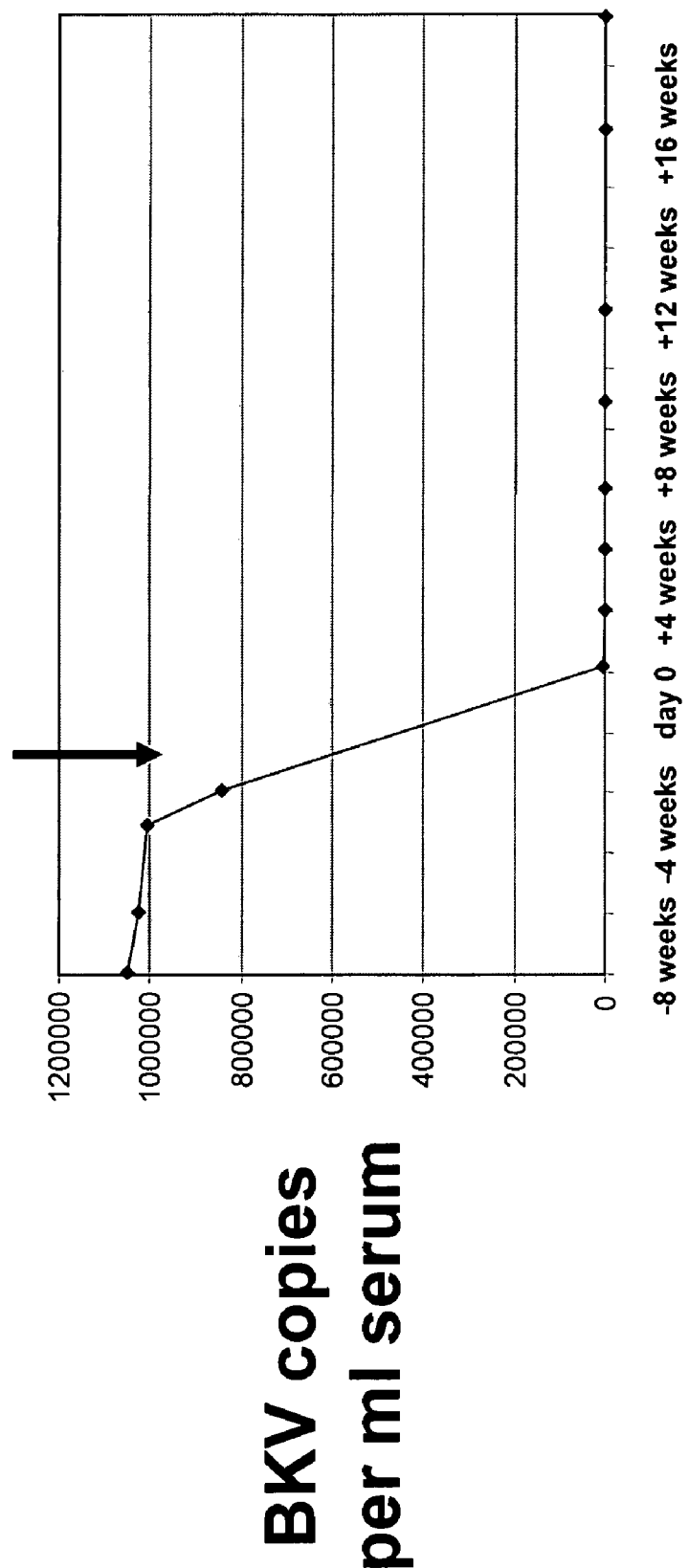
Figure 1D:
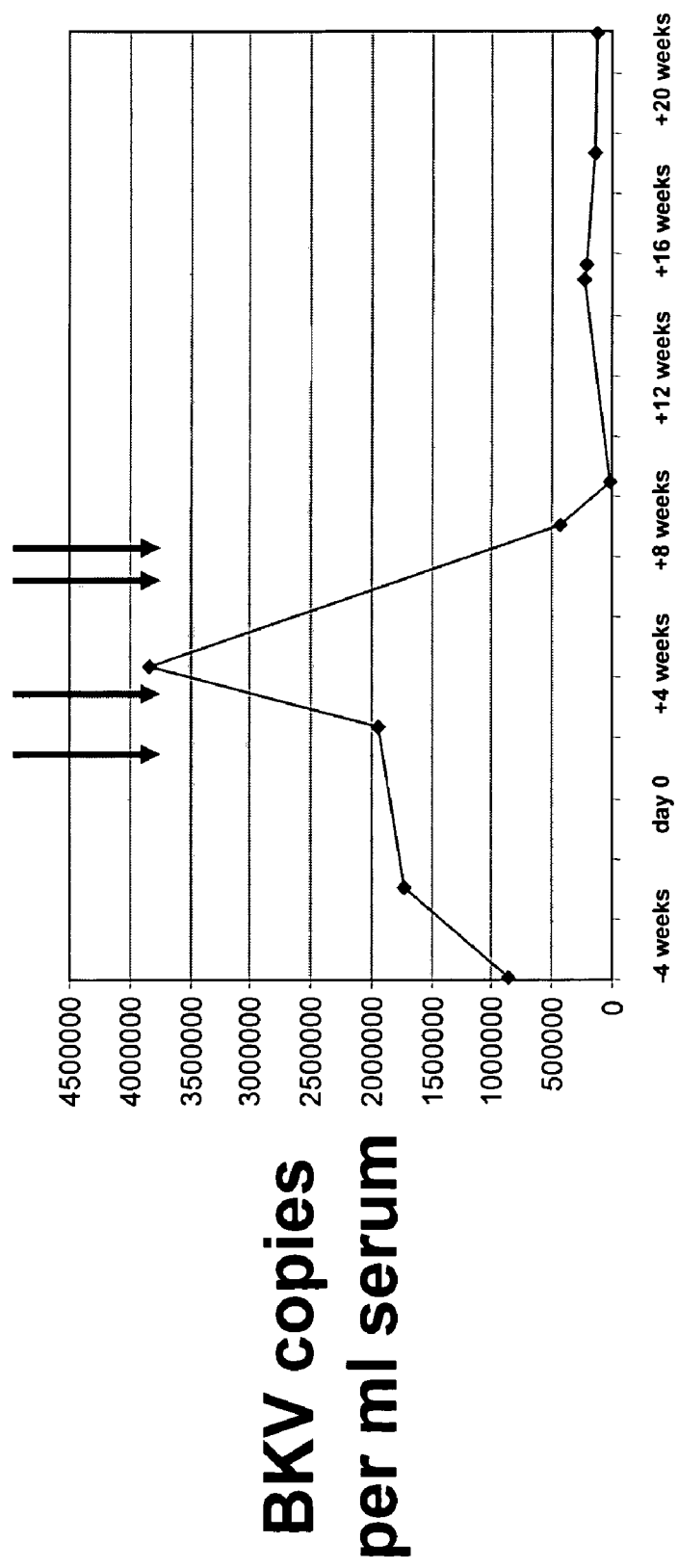
Figure 1E:
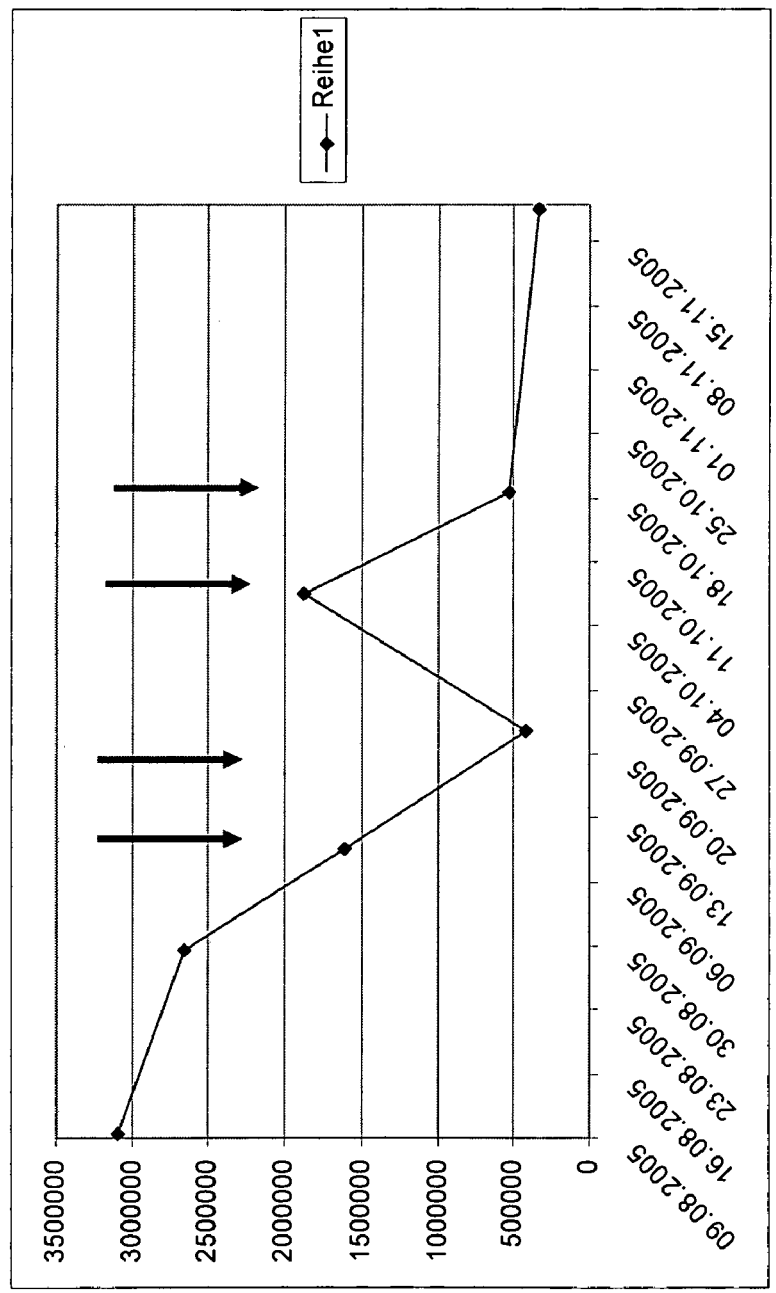

The present invention relates to uses of a B-cell-depleting antibody.

Polyoma viruses are DNA-based viruses without a lipoprotein envelope. They are potentially oncongenic and are often acquired early in the life of an individual where they persist as latent infections in a host without actually causing a disease. Polyoma viruses have been identified for a number of hosts, including birds, monkeys, rodents, bovines and humans. In humans there are two Polyoma viruses: JC virus and BK virus: The JC virus can infect the respiratory system, kidneys or brain. In the latter case this causes the disease progressive multifocal leucoencephalopathy (PML). The BK virus produces a mild respiratory infection and may affect the kidneys of immune suppressed transplant patients. Both viruses are widely spread. For example 80% of the adult population in the United States have antibodies to BK and JC.

Viral complications are rather common after solid organ (SOT) and bone marrow/stem cell (BMT) transplantations. The reason for the increase in incidences and severity of viral diseases is a diminished immunity due to medical immune suppression (in the case of SOT) or a lymphopenic state (in the case of BMT). Amongst other viruses, active polyoma virus infections are rather common in transplanted patients. A polyoma virus infection frequently results in a decreased graft function or a graft loss, for example after kidney transplantation. After bone marrow/stem cell transplantation (BMT), polyoma virus infection may result in a hemorrhagic cystitis. Moreover, a polyoma virus infection may also lead to central nervous complications, for example in patients having a deficient or suppressed immune system, such as HIV patients or patients having received immuno suppressant medication, where the polyoma virus infection may cause progressive multifocal leucoencephalopathy (PML).

BK virus associated nephropathy has been increasingly recognized as an important contributor to morbidity in renal allograph recipients. Manna et al. (American Transplant Congress, Poster Board # 138, May 16, 2004) have shown that a significant proportion (up to 23%) of patients with BK virus can have a coexisting JCV infection (JC virus). The JCV infection, however, may have a course that is independent of BKV infection. Such coexistent and/or independent JCV infection may contribute to the clinical course of polyoma virus associated syndromes, including response to therapy.

Randhawa et al (Transplantation, 2003; 71: 1300-1303) have shown that JCV is detectable in a subset of renal allograph kidneys with polyoma virus associated nephropathy.

A review of polyoma virus infections can be found in Kwak et al (Clinical Infectious Diseases, 2006; 35: 1081-1087). U.S. Pat. No. 6,605,602 discloses the possibility of treating polyoma virus associated nephropathy (PVAN), in particular BK virus associated nephropathy (BKVN) by cidofovir. Cidofovir is the name for (S)-1-3-hydroxy-2phosphonyl-methoxypropyl)cytosine), which is an acyclic nucleotide phosphonate with a broad-spectrum activity against a wide variety of DNA-viruses. It is reportedly effective in patients diagnosed with progressive multifocal leucoencephalopathy. However, cidofovir is nephrotoxic and therefore is contraindicated in patients with impaired renal functions. Accordingly, there remains a need in the art for alternative treatments for polyoma virus infections. Accordingly, it has been an object of the present invention to provide for means that allow the treatment of a polyoma virus infection. Moreover, it was an object of the present invention to provide for means that allow the reduction of polyoma virus titer in a significant, prolonged and measurable manner.

All these objects are solved by use of a B-cell depleting antibody for the manufacture of a medicament for the treatment of a polyoma virus infection.

In one embodiment, said polyoma virus infection is in a patient having a nephropathy, preferably a polyoma virus associated nephropathy.

Preferably, said nephropathy is selected from the group comprising glomerulonephritis, interstitial nephritis, and pyelonephritis.

In one embodiment, said polyoma virus infection is in a patient having a hemorrhagic cystitis, preferably a polyoma virus associated hemorrhagic cystitis.

In one embodiment, said polyoma virus infection is in a patient having received a transplantation or being supposed to receive transplantation, wherein, preferably, said transplantation is a solid organ transplantation or a bone marrow transplantation or a stem-cell transplantation.

In one embodiment, said transplantation is a solid organ transplantation, preferably a renal transplantation.

In another embodiment said transplantation is a bone marrow transplantation or a stem cell transplantation.

In one embodiment, said polyoma virus infection is in a patient having progressive multifocal leukoencephalopathy, wherein, preferably, said progressive multifocal leucoencephalopathy is in a patient having a deficient immune system, wherein, more preferably, said deficient immune system is an immune system suppressed by medication or is an immune system deficient because of an infection by human immune deficiency virus (HIV) or because of an affection by systemic lupus erythematosus.

In one embodiment, said B-cell depleting antibody is an anti-CD20-antibody, wherein, preferably, said B-cell depleting antibody is selected from the group comprising rituximab, and antibodies directed against B-cell surface molecules, more preferably antibodies directed against B-cell specific surface molecules such as CD19, CD20, CD22, CD72, CD79a, and CD79b.

In one embodiment, said B-cell depleting antibody is administered in a dose of 1 mg to 1 g, preferably 100 mg to 800 mg, more preferably 250 mg to 750 mg, most preferably 300 mg to 500 mg. Preferably, said B-cell depleting antibody is administered in one dose every 2-20 days, preferably one dose every 7-14 days.

In another embodiment, said B-cell depleting antibody is administered in one dose every 1-3 days, wherein preferably it is administered in one dose daily.

In one embodiment, said B-cell depleting antibody is administered in 1-20 doses in total, preferably in 1-10 doses, more preferably 1-8 doses, and most preferably 1-4 doses in total. The term "in total", as used in this context, refers to an entire course of treatment.

In one embodiment, said administration is systemical, preferably via injection or infusion, more preferably an intravenous injection or infusion.

Preferably, said administration results in a reduction of virus titre by 1-4 log DNA copies/ml serum or urine, as measured by PCR, preferably real-time PCR.

In one embodiment, said B-cell depleting antibody is administered to a patient in need thereof, and said administration results in a prevention of a deterioration of the function of the transplanted solid organ or bone marrow or stem cells, or in the prevention of a rejection thereof after transplantation, wherein, preferably, said patient is a non-responder or a relapser after a previous treatment by cidofovir and/or hyperimmune globulins.

The term "a patient in need thereof", as used herein, is meant to refer to any patient whose condition benefits from administration of a B-cell-depleting antibody.

Preferably such "patient in need thereof" is a patient having a polyoma virus infection and, additionally, one condition selected from the following: nephropathy, in particular glomerulonephritis, interstitial nephritis and pyelonephritis; haemorrhagic cystitis; a condition wherein the patient has received a transplantation or is supposed to receive a transplantation, in particular a solid organ transplantation, a bone marrow transplantation or a stem-cell transplantation; progressive multi-focal leucoencephalopathy, in particular a progressive multifocal leucoencephalopathy in a patient having a deficient immune system, wherein more preferably, the deficient immune system is an immune system suppressed by medication or is an immune system deficient because of an infection by Human Immune Deficiency Virus (HIV) or because of an affection by systemic lupus erythemathosus.

The phrase "wherein said administration results in a prevention of a deterioration of the function of the transplanted solid organ or bone marrow or stem cells", as used herein, is meant to refer to the fact that the administration of a B-cell-depleting antibody leads to such prevention of a deterioration of the function of the transplanted solid organ or bone marrow or stem cells, or leads to the prevention of a rejection of such transplant after transplantation.

In one embodiment, said B-cell depleting antibody is administered prior to or after said solid organ transplantation or said bone marrow transplantation or said stem cell transplantation.

In one embodiment, said B-cell depleting antibody is administered in combination with other medication, preferably in combination with antiviral medication, such as cidofovir or hyperimmune globulins, and/or with anti-inflammatory agents, such as steroids or immunosuppressants.

The present disclosure also relates to methods of treatment of a polyoma virus infection, using a B-cell depleting antibody, wherein the antibody, its administration, the patient and the treatment is as defined in any of the foregoing embodiments and/or in the description hereafter.

The term "polyoma virus infection", as used herein is meant to signify any state of a patient, preferably a human patient, wherein either nucleic acid copies of a polyoma virus and/or anti-bodies against a polyoma virus are detectable in a body fluid of such affected individual, preferably in the serum or the urine. Moreover, the term "polyoma virus infection" is meant to include an "active Polyoma virus infection" which is characterized by the virus actively replicating and concomitantly deteriorating a graft function or contributing to a graft loss after an organ transplantation. The "treatment" of such an "active polyoma virus infection" is therefore aimed at the prevention of such deterioration of graft function and/or aimed at the prevention of graft loss. As used herein, the term "polyoma virus associated nephropathy/hemorrhagic cystitis" is meant to signify and include any nephropathy/hemorrhagic cystitis that is accompanied by polyoma virus infection, without proof or evidence for the Polyoma virus infection necessarily being the causative agent or sole causative agent of such nephropathy/hemorrhagic cystitis. Both terms "polyoma virus associated nephropathy" and "polyoma virus associated hemorrhagic cystitis" are commonly used in the art and are therefore well-understood by someone skilled in the art (see also the above discussion of prior art).

The term "progressive multifocal leucoencephalopathy", as used herein, is meant to signify a humane polyoma virus associated disorder of the nervous system which is characterized by a demyelination or distruction of the myelin sheath. Symptoms of progressive multifocal leucoencephalopathy (PML) include mental deterioration, vision loss, speech disturbances, ataxia, paralysis and, ultimately coma reflecting the multifocal distribution of brain leasons. It is currently believed that the main causative aident of PML is the human JC virus.

The term "B-cell-depleting antibody" is meant to signify any antibody which contributes to a reduction of B-cells in the blood. Preferably, it is meant to signify an antibody that binds to B-cells in order to thereby recruit the body's natural defences to attack and kill the target B-cells. Preferably such a B-cell-depleting antibody is a monoclonal antibody. B-cell-depleting antibodies are commercially available, such as rituximab which is available under the trademark name "MabThera™". Other useful B-cell depleting antibodies are such antibodies being directed against B-cell surface molecules, more preferably B-cell specific surface molecules such as CD19, CD20, CD22, CD72, CD79a, CD79b.

Moreover, reference is made to FIGS. 1a)-1e) which show the time course of the titer of polyoma DNA-copies in the serum of five individual patients. In these figures, the number of DNA-copies of polyoma virus, as determined by real-time-PCR, per ml serum is plotted vs. time. An arrow indicates the administration of one dose (375 mg) of rituximab.

Moreover, reference is made to the following example, which is meant to illustrate, not to limit the present invention.

EXAMPLE

Five patients having an active Polyoma virus infection after kidney transplantation, who were non-responders to a previous treatment with current therapeutic approaches against Polyoma virus infections, such as hyperimmune globulins and/or cidofovir, were treated as follows: These patients were given 1 to 4 doses of rituximab (each dose comprising 375 mg rituximab) by intravenous infusion/injection. Prior to such rituximab treatment all patients had more than 10 000 Polyoma DNA copies per ml serum. Upon rituximab treatment, the virus titer was reduced by 1-4 log. These results demonstrate that a therapy of a Polyoma virus infection is possible and highly successful using a B-cell-depleting antibody such as rituximab. 5 months after the end of the treatment 3 patients still had no detectable virus nucleic acid. Similar results have also been achieved in a further experimental series with the same experimental design as above (results not shown).

Further Experimental Details

Patients

Renal transplant patients with high level of BKV load, clinical and histological signs for BKVAN (polyoma BK virus-associated nephropathy) were included in the study. The patients underwent renal transplantation in the University Hospital Charite. The study was approved by the local hospital ethical committee, and informed consent was obtained from all subjects. Patients were followed for at least 7 months after the completion of the infusion. The mean age of the recipients was 45.2 years ranged from 37 to 53 years. 67% were males, and 33% were females. All but one patient received first cadaver kidney transplants. One patient received her second transplant. Mean transplant age was 23.3±21.4 months (range from 8 to 67 months). All but one patient were under standard triple maintenance immunosuppressive regimen (tacrolimus/ciclosporin A, methylprednisone, and MMF). One patient was treated by Campath (20 mg), Methylprednisolon, and FK 506 (tacrolimus) (target blood level 10 ng/mL). None of the patients had a history of previous rejection episodes or any infections.

Treatment Protocol

The maintenance immunosuppression was changed within one week after the histological diagnosis of PVAN (Polyoma virus-associated nephropathy): tacrolimus was replaced by Ciclosporin A with the trough level targeted at 100-150 mg/mL. Mycophenilate mofetil was replaced by azathioprin (75 mg/day). Methylprednisone maintained unchanged at 4-8 mg/day. There were no other changes in the immunosuppressive regimen. Rituximab was given at a dose of 375 mg/m$^2$ weekly for 3 weeks. There was no additional therapy with any other aniviral drugs.

Analysis of BKV Load in Serum

The analysis of BKV load in serum was performed in all transplant patients every 4 weeks during the first post-transplant year (or every three months after the first post-transplant year) routinely or in all patients with increased creatinine level as part of the assessment for renal dysfunction. BKV-DNA copies were measured by TaqMan Real Time PCR as described previously (Hammer, 2006, Am. J. Transplant., 6(3):625-631). DNA was isolated from serum using a QIAamp DNA Mini Kit (Qiagen Corp., Hilden, Gemany) according to manufacturer's instructions.

The features of the present invention disclosed in the specification, the claims and/or in the accompanying drawings, may, both separately, and in any combination thereof, be material for realizing the invention in various forms thereof.

The invention claimed is:

1. A method of treatment of a polyoma virus infection using a-B-cell depleting antibody, wherein said polyoma virus infection is in a patient having a nephropathy, preferably a polyoma virus associated nephropathy, comprising administering said B-cell depleting antibody to said patient in a dose of about 1 mg to 1 g.

2. The method according to claim 1, wherein said nephropathy is selected from the group comprising glomerulonephritis, interstitial nephiritis, and pyelonephritis.

3. The method according to claim 1, wherein said polyoma virus infection is in a patient having a hemorrhagic cystitis, preferably a polyoma virus associated hemorrhagic cystitis.

4. The method according to claim 1, wherein said polyoma virus infection is in a patient having received a transplantation or being supposed to receive transplantation.

5. The method according to claim 4, wherein said transplantation is a solid organ transplantation or a bone marrow transplantation or a stem-cell transplantation.

6. The method according to claim 4, wherein said transplantation is a solid organ transplantation, preferably a renal transplantation.

7. The method according to claim 4, wherein said transplantation is a bone marrow transplantation or a stem cell transplantation.

8. The method according to claim 1, wherein said polyoma virus infection is in a patient having progressive multifocal leukoencephalopathy.

9. The method according to claim 8, wherein said progressive multifocal leucoencephalopathy is in a patient having a deficient immune system.

10. The method according to claim 9, wherein said deficient immune system is an immune system suppressed by medication or is an immune system deficient because of an infection by human immune deficiency virus (HIV) or because of an affection by systemic lupus erythematosus.

11. The method according to claim 1, wherein said B-cell depleting antibody is an anti-CD20-antibody.

12. The method according to claim 11, wherein said B-cell depleting antibody is selected from the group comprising rituximab and antibodies directed against B-cell surface molecules, more preferably antibodies directed against B-cell specific surface molecules, such as CD19, CD20, CD22, CD72, CD79a, CD79b.

13. The method according to claim 1, wherein said B-cell depleting antibody is administered in a dose of 100 mg to 800 mg, more preferably 250 mg to 750 mg, most preferably 300 mg to 500 mg.

14. The method according to claim 13, wherein said B-cell depleting antibody is administered in one dose every 2-20 days, preferably one dose every 7-14 days.

15. The method according to claim 13, wherein said B-cell depleting antibody is administered in one dose every 1-3 days.

16. The method according to claim 13, wherein said B-cell depleting antibody is administered in 1-20 doses in total, preferably in 1-10 doses, more preferably 1-8 doses, and most preferably 1-4 doses in total.

17. The method according to claim 13, wherein said administration is systemical, preferably via injection or infusion, more preferably an intravenous injection or infusion.

18. The method according to claim 13, wherein said administration results in a reduction of virus titre by 1-4 log DNA copies/ml serum or urine, as measured by PCR, preferably real-time PCR.

19. The method according to claim 5, wherein said B-cell depleting antibody is administered to a patient in need thereof, and said administration results in a prevention of a deterioration of the function of the transplanted solid organ or bone marrow or stem cells, or in the prevention of a rejection thereof after transplantation.

20. The method according to claim 19, wherein said patient is a non-responder or a relapser after a previous treatment by cidofovir and/or hyperimmune globulins.

21. The method according to claim 19, wherein said B-cell depleting antibody is administered prior to or after said solid organ transplantation or said bone marrow transplantation or said stem cell transplantation.

22. The method according to claim 1, wherein said B-cell depleting antibody is administered in combination with other medication, preferably in combination with antiviral medication, such as cidofovir or hyperimmune globulins, and/or with anti-inflammatory agents, such as steroids or immune-suppressants.

* * * * *